United States Patent
Wada et al.

(10) Patent No.: US 10,980,458 B2
(45) Date of Patent: Apr. 20, 2021

(54) PHOTOACOUSTIC APPARATUS AND CONTROL METHOD THEREOF

(71) Applicant: CANON KABUSHIKI KAISHA, Tokyo (JP)

(72) Inventors: Yoshiko Wada, Kyoto (JP); Takuji Oishi, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 199 days.

(21) Appl. No.: 16/176,475

(22) Filed: Oct. 31, 2018

(65) Prior Publication Data
US 2019/0069825 A1 Mar. 7, 2019

Related U.S. Application Data

(63) Continuation of application No. 14/007,447, filed as application No. PCT/JP2012/059298 on Mar. 29, 2012, now Pat. No. 10,149,639.

(30) Foreign Application Priority Data

Apr. 6, 2011 (JP) ................................ 2011-084794

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/0095* (2013.01); *A61B 5/02007* (2013.01);
(Continued)

(58) Field of Classification Search
None
See application file for complete search history.

(56) References Cited

U.S. PATENT DOCUMENTS

| 6,058,218 A | 5/2000 | Cline |
| 2005/0085725 A1 | 4/2005 | Nagar et al. |

(Continued)

OTHER PUBLICATIONS

X. Wang, et al., "Noninvasive imaging of hemoglobin concentration and oxygenation in the rat brain using high-resolution photoacoustic tomography", J. Biomed. Opt., 11(2), pp. 024015-1-024015-9 (Mar./Apr. 2006).

(Continued)

*Primary Examiner* — Marjan Fardanesh
(74) *Attorney, Agent, or Firm* — Venable LLP

(57) ABSTRACT

A used photoacoustic apparatus includes: a light source capable of individually emitting light having a first wavelength at which absorption coefficients of oxyhemoglobin and deoxyhemoglobin are equal and light having a second wavelength; an acoustic detector that receives acoustic waves generated when the light having the first and second wavelengths is absorbed by an object; an absorption coefficient distribution generator that determines absorption coefficient distributions of an object interior; a blood vessel position determining unit that determines a blood vessel position from an absorption coefficient distribution corresponding to the first wavelength; an organism characteristics distribution calculator that determines an organism characteristics distribution from the absorption coefficient distributions; and a trimming unit that trims the organism characteristics distribution in accordance with the blood vessel position.

27 Claims, 11 Drawing Sheets

(51) Int. Cl.
*A61B 5/02* (2006.01)
*A61B 5/145* (2006.01)
*G01N 21/17* (2006.01)

(52) U.S. Cl.
CPC .......... *A61B 5/14532* (2013.01); *A61B 5/489* (2013.01); *G01N 21/1702* (2013.01); *A61B 5/14542* (2013.01)

(56) References Cited

U.S. PATENT DOCUMENTS

| 2010/0020230 | A1 | 1/2010 | Suzuki |
| 2010/0331707 | A1* | 12/2010 | Fukutani .............. A61B 5/0073 600/476 |
| 2012/0289812 | A1 | 11/2012 | Oishi |
| 2013/0160558 | A1 | 6/2013 | Oishi |
| 2014/0100438 | A1 | 4/2014 | Wada |
| 2014/0187924 | A1 | 7/2014 | Oishi |

OTHER PUBLICATIONS

H.F. Zhang, "Functional Photoacoustic Microscopy", Dissertation, Texas A & M University (Aug. 2006).

H.F. Zhang et al., "Imaging of Hemoglobin Oxygen Saturation Variations in Single Vessels in vivo Using Photoacoustic Microscopy", Applied Physics Letters 90, 053901 (Jan. 29, 2007).

J. Laufer et al., "Quantatitive in vivo Measurements of Blood Oxygen Saturation Using Multiwavelength Photoacoustic Imaging", Proceedings of SPIE, vol. 6437, 64371Z (2007).

D. Bauer et al., "In vivo Multi-Modality Photoacoustic and Pulse Echo Tracking of Prostate Tumor Growth Using a Window Chamber", Proc. of SPIE, vol. 7564, 75643B (2010).

S Hu et al., "Photoacoustic Imaging and Characterization of the Microvasculature", Journal of Biomedical Optics, vol. 15, No. 1, 011101 (Jan. 21, 2010).

* cited by examiner

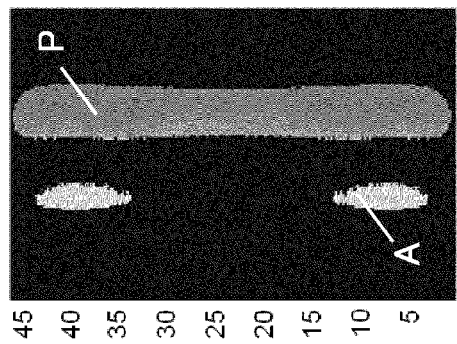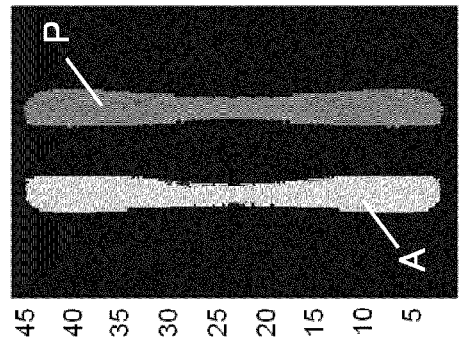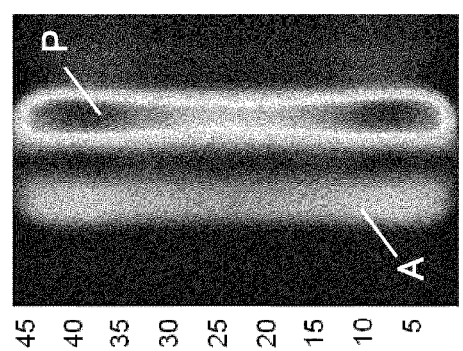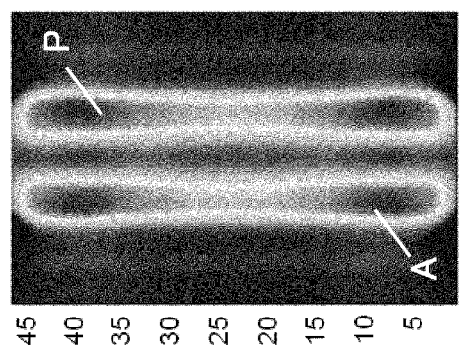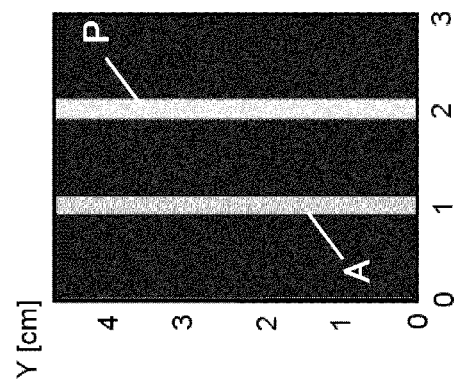

PHOTOACOUSTIC APPARATUS AND CONTROL METHOD THEREOF

This is a continuation of U.S. patent application Ser. No. 14/007,447, filed on Sep. 25, 2013, which is the national stage entry under 35 U.S.C. § 371 of International Patent Application No. PCT/JP2012/059298, filed Mar. 29, 2012, which claims the benefit of Japanese Patent Application No. 2011-084794, filed on Apr. 6, 2011, all of which are hereby incorporated by reference herein in their entireties.

TECHNICAL FIELD

The present invention relates to a photoacoustic apparatus and a control method thereof.

BACKGROUND ART

A photoacoustic apparatus used for medical diagnoses, for example, has been proposed as an apparatus that obtains information from an interior of a test subject (an object) using ultrasound waves (acoustic waves). The photoacoustic apparatus irradiates the object with laser pulsed light, and receives photoacoustic waves generated when tissue in the object absorbs energy from the irradiation light in a plurality of locations surrounding the object. Temporal variation in the received acoustic waves is then subjected to mathematical analysis processing, or in other words image reconstruction. As a result, information relating to optical characteristic values of the object interior can be visualized in two or three dimensions. Techniques of this type are also known as photoacoustic tomography (PAT).

An intensity of the acoustic waves generated from the internal tissue of the object varies according to an intensity of the irradiation light reaching the tissue and an absorption coefficient relative to a wavelength of the irradiation light. Many types of light-absorbing tissue, such as melanin, fat, water, hemoglobin, cholesterol, and collagen exist in the object, and each type of tissue has a different absorption coefficient relative to the wavelength. Therefore, when measurement is performed at different wavelengths and an image is reconstructed, different absorption coefficient distribution images are obtained even with respect to identical tissue in a single object.

A method of determining a blood oxygen saturation of the object using wavelength-dependent absorption coefficient distribution images is known. Two types of hemoglobin (oxyhemoglobin and deoxyhemoglobin) existing in blood vessels of the object have different absorption spectra, and therefore different absorption coefficient distribution images are obtained when measurement is performed at different wavelengths. A distribution ratio between oxyhemoglobin and deoxyhemoglobin (i.e. the oxygen saturation of the blood) can be calculated from these absorption coefficient distribution images. In NPL 1, for example, an oxygen saturation of a blood vessel is obtained from a reconstructed image using four wavelengths (578 nm to 598 nm).

CITATION LIST

Non Patent Literature

NPL 1: FUNCTIONAL PHOTOACOUSTIC MICROSCOPY, HAO ZHANG, texas A&M University, August 2006

SUMMARY OF INVENTION

Technical Problem

As shown in FIG. 6, however, the four wavelengths (578 nm, 584 nm, 590 nm, 596 nm) used in NPL 1 are in a wavelength region where absorption coefficients μa of hemoglobin, epidermis, and dermis serving as measurement subjects are high. Therefore, the irradiation light only reaches approximately several millimeters under a skin surface, making it impossible to measure a blood vessel in a deep portion of the object interior.

Further, a formula for calculating the oxygen saturation includes a quotient calculation for the results obtained from the different absorption coefficient distribution images, and therefore noise levels of the absorption coefficient distribution images and positional deviation of an absorber caused by bodily movement of the object greatly affect a noise level and an error in the oxygen saturation result.

As a method of reducing the visibility of noise in the oxygen saturation due to noise in the absorption coefficient distribution images, the oxygen saturation result may be displayed after being trimmed in a blood vessel position. Here, the blood vessel position is assumed to be a location where the absorption coefficient distribution of hemoglobin exists. As is evident from the absorption coefficient spectra of the two types of hemoglobin shown in FIG. 7, however, at a wavelength (756 nm, for example) where the two absorption coefficients are different, the absorption coefficient of an artery is low while the absorption coefficient of a vein is high.

When a position having an absorption coefficient of at least a certain numerical value (at least 30% when a strength of a vein is set at 100%) on the absorption coefficient distribution is set as a blood vessel, a value having a different strength is calculated with respect to a blood vessel having an identical thickness, as shown in FIG. 8, and therefore the thickness of the blood vessel appears to be different. Hence, when the oxygen saturation is trimmed using the absorption coefficient distribution, blood vessels having an identical thickness are displayed as blood vessels having different thicknesses on an oxygen saturation distribution image, as shown in FIGS. 5B and 5C (where P indicates a vein and A indicates an artery).

Meanwhile, when bodily movement occurs in the object, as shown in FIG. 9, the position of the absorption coefficient distribution varies. The oxygen saturation is calculated using an absorption coefficient of an identical position, and therefore variation in the absorption coefficient distribution due to bodily movement affects the oxygen saturation calculation result. When the bodily movement is greater than the thickness of the blood vessel, the oxygen saturation calculation result becomes senseless.

The present invention has been designed in consideration of the problems described above, and an object thereof is to provide a photoacoustic apparatus capable of generating image data from which a relationship between an organism characteristics distribution of an object and a position of a blood vessel can be understood easily, and reducing an effect of a deviation in a measurement position.

Solution to Problem

The present invention provides a photoacoustic apparatus comprising:

a light source capable of individually emitting light having a first wavelength at which absorption coefficients of oxyhemoglobin and deoxyhemoglobin are equal and light having a second wavelength that is different from the first wavelength;

an acoustic detector that receives acoustic waves generated when the light having the first wavelength and the light having the second wavelength are respectively absorbed by an object, and converts the received acoustic waves into electric signals;

an absorption coefficient distribution generator that determines absorption coefficient distributions of an object interior by using the electric signals;

a blood vessel position determining unit that determines a blood vessel position in the object interior from an absorption coefficient distribution corresponding to the first wavelength;

an organism characteristics distribution calculator that determines an organism characteristics distribution of the object interior from the absorption coefficient distributions corresponding to the light having the first wavelength and the light having the second wavelength; and a trimming unit that trims the organism characteristics distribution in accordance with the blood vessel position determined by the blood vessel position determining unit.

The present invention also provides a control method for a photoacoustic apparatus, the method comprising:

an absorption coefficient distribution calculating step in which an information processing device determines absorption coefficient distributions of an interior of an object on the basis of acoustic waves generated by the object when the object is irradiated individually with light having a first wavelength at which absorption coefficients of oxyhemoglobin and deoxyhemoglobin are equal and light having a second wavelength that is different from the first wavelength;

a blood vessel position determining step in which the information processing device determines a blood vessel position of the object interior from an absorption coefficient distribution corresponding to the first wavelength;

an organism characteristics distribution calculating step in which the information processing device determines an organism characteristics distribution of the object interior from the absorption coefficient distributions corresponding to the light having the first wavelength and the light having the second wavelength; and a trimming step in which the information processing device trims the organism characteristics distribution in accordance with the blood vessel position determined in the blood vessel position determining step.

Advantageous Effects of Invention

According to the present invention, a photoacoustic apparatus capable of measuring an organism characteristics distribution of a deep portion of an object, generating image data from which a relationship between the measured organism characteristics distribution and a position of a blood vessel can be understood easily, and reducing an effect of a deviation in a measurement position can be provided.

Further features of the present invention will become apparent from the following description of exemplary embodiments with reference to the attached drawings.

BRIEF DESCRIPTION OF DRAWINGS

FIGS. 5A to 5E are views showing measurement results according to the first embodiment;

DESCRIPTION OF EMBODIMENTS

Embodiments of a photoacoustic apparatus according to the present invention will be described below with reference to the drawings. In the following description, a photoacoustic diagnosis apparatus that forms an image of an interior of an object using a photoacoustic tomography technique will be cited as an example.

The photoacoustic apparatus according to the present invention irradiates an object with light (electromagnetic waves) to receive acoustic waves generated in the object, and uses a photoacoustic effect to obtain object information in the form of image data. The acoustic wave is typically an ultrasound wave, but includes elastic waves known as sound waves, ultrasound waves, acoustic waves, photoacoustic waves, and optical ultrasound waves.

Figure 1:
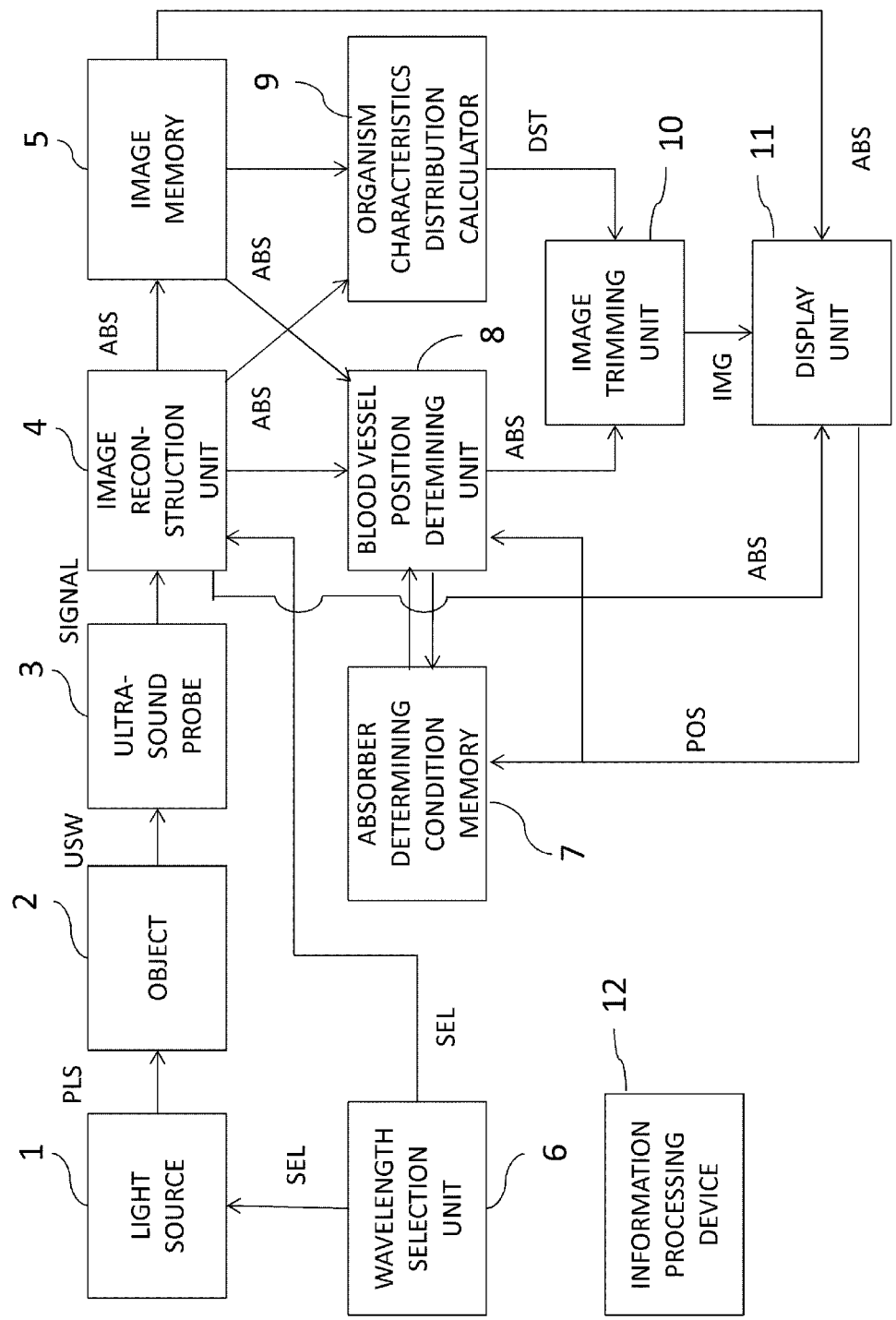
FIG. 1 is a block diagram of a photoacoustic apparatus according to the present invention.

FIG. 1 is a block diagram of the photoacoustic diagnosis apparatus according to this embodiment.

The photoacoustic diagnosis apparatus includes a light source 1, an ultrasound probe 3, an image reconstruction unit 4, an image memory 5, a wavelength selection unit 6, an absorber determining condition memory 7, a blood vessel position determining unit 8, an organism characteristics distribution calculator 9, an image trimming unit 10, a display unit 11, and an information processing device 12. Operations and functions of the respective blocks will be described in detail below. An object 2 is a measurement subject such as an organism, for example.

(Operation of Photoacoustic Diagnosis Apparatus)

Figure 2:
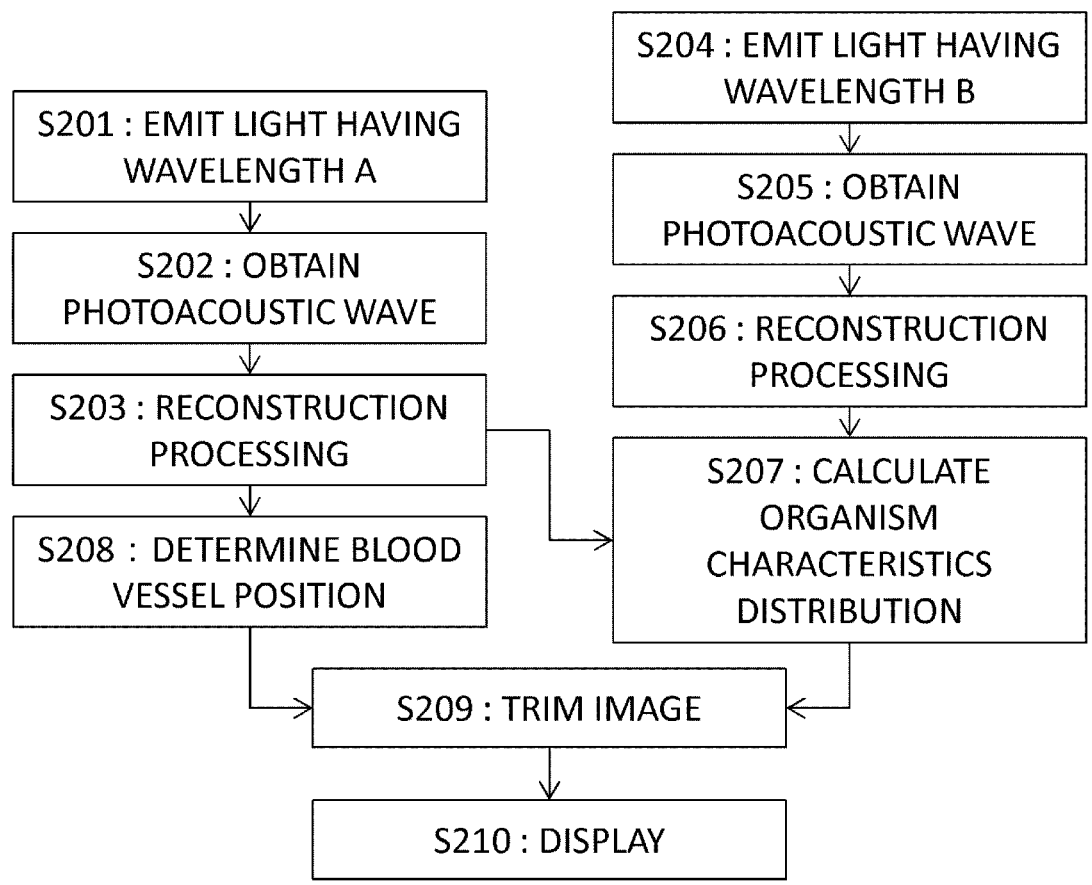
FIG. 2 is a flowchart showing processing according to a first embodiment.

FIG. 2 is a flowchart of a first embodiment.

In Step S201, the photoacoustic diagnosis apparatus irradiates the object 2 with pulsed light from the light source 1. The pulsed light is in a wavelength region of at least 700 nm, and has a wavelength A at which absorption coefficients of two types of hemoglobin (oxyhemoglobin and deoxyhemoglobin) are equal. The pulsed light is absorbed by a light absorber in the object 2, whereby a photoacoustic wave constituting an ultrasound wave (an acoustic wave) is generated. Note that in the present invention, "the absorption coefficients are equal" includes not only a case in which the absorption coefficients are perfectly equal, but also a case in which the absorption coefficients are substantially equal. The respective absorption coefficients of the two types of hemoglobin may be considered substantially equal when a difference between the two absorption coefficients is no greater than 10%.

In Step S202, the generated photoacoustic wave is obtained by a plurality of elements included in the ultrasound probe 3 and converted into an electric signal (an element signal). The electric signal is then subjected to signal processing such as amplification and digital conversion as required.

In Step S203, the amplified and digitally converted electric signal is subjected to image reconstruction processing by the image reconstruction unit 4, whereby an absorption coefficient distribution image A is created as a three-dimensional image showing an absorption coefficient distribution. The absorption coefficient distribution image A is stored temporarily in the image memory 5.

In Steps S204, S205, and S206, the object is irradiated with pulsed light having a different wavelength B to the wavelength A, whereupon an absorption coefficient distribution image B is created by the image reconstruction unit 4 from an electric signal based on a generated photoacoustic wave.

In Step S207, the organism characteristics distribution calculator 9 generates an organism characteristics distribution using the absorption coefficient distribution image A corresponding to the wavelength A, which is stored in the image memory 5, and the absorption coefficient distribution image B corresponding to the wavelength B. The organism characteristics distribution is an oxygen saturation distribution or a glucose distribution.

In Step S208, a position of a blood vessel included in the absorption coefficient distribution image A obtained at the wavelength A where the absorption coefficients of the two types of hemoglobin are substantially equal is determined by the blood vessel position determining unit 8. Conditions required to determine the blood vessel position on the image are stored rewritably in the absorbent determining condition memory 7.

In Step S209, the image trimming unit 10 creates an image on which the oxygen saturation distribution or other organism characteristics distribution is emphasized in the blood vessel position diagnosed by the blood vessel position determining unit 8.

In Step S210, the absorption coefficient distribution image and the oxygen saturation image created by the image trimming unit 10 are displayed by the display unit 11. Further, the emphasized oxygen saturation image and the absorption coefficient distribution image A may be displayed in overlapped form.

Here, the order of measurement at the wavelength A, performed in S201 to S203, and measurement at the wavelength B, performed in S204 to S206, may be reversed. Further, S204 and S205 may be performed after S201 and S202, followed by Steps S203 and S206 in which reconstruction is performed. The order of the organism characteristics calculation of S207 and the blood vessel position determination of S208 may also be reversed.

Referring back to FIG. 1, the operations and functions of the respective blocks will now be described in detail.

(Light Source)

Figure 6:
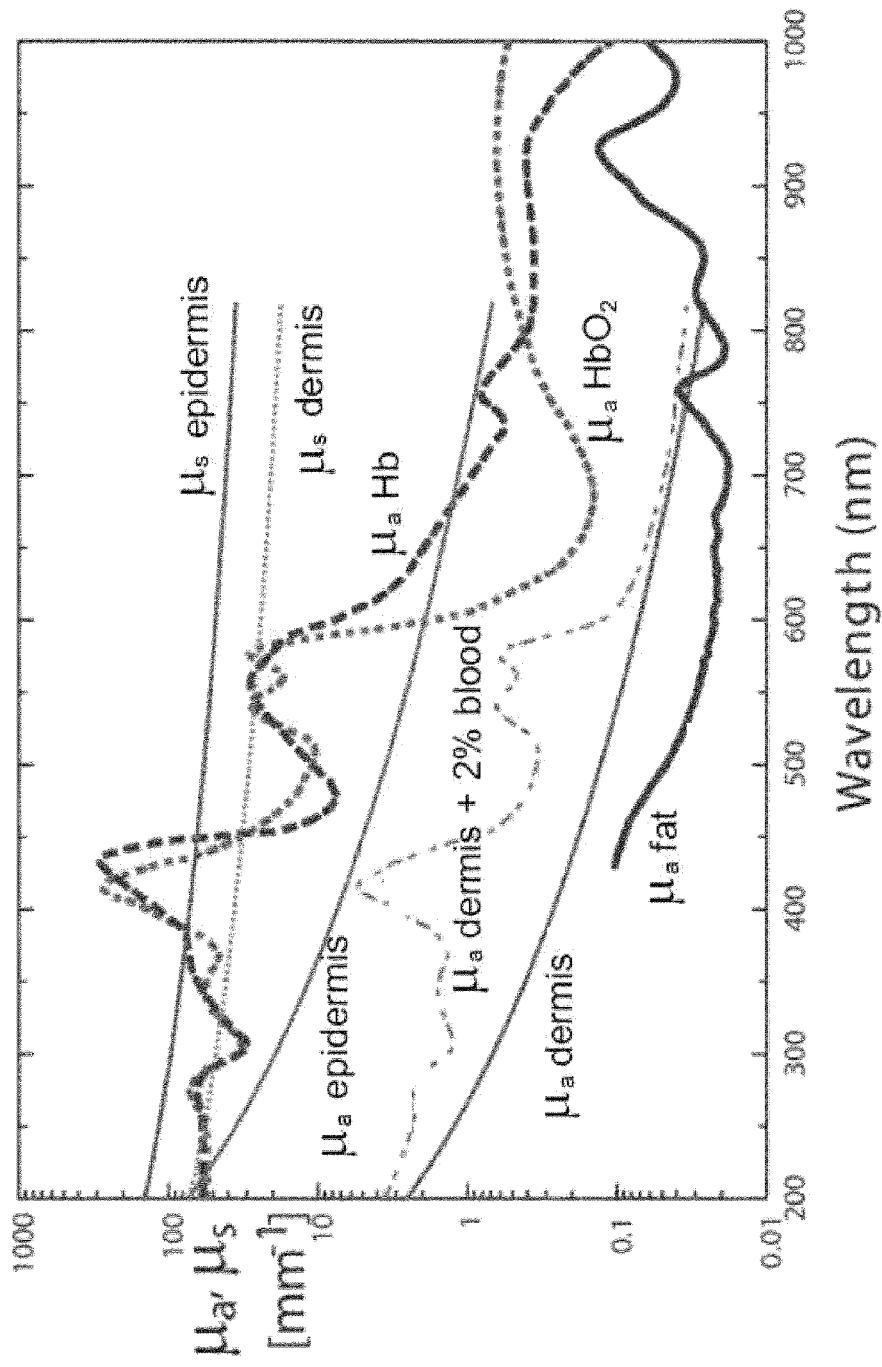
FIG. 6 is a view showing absorption spectra of compositional substances of an object.
Figure 7:
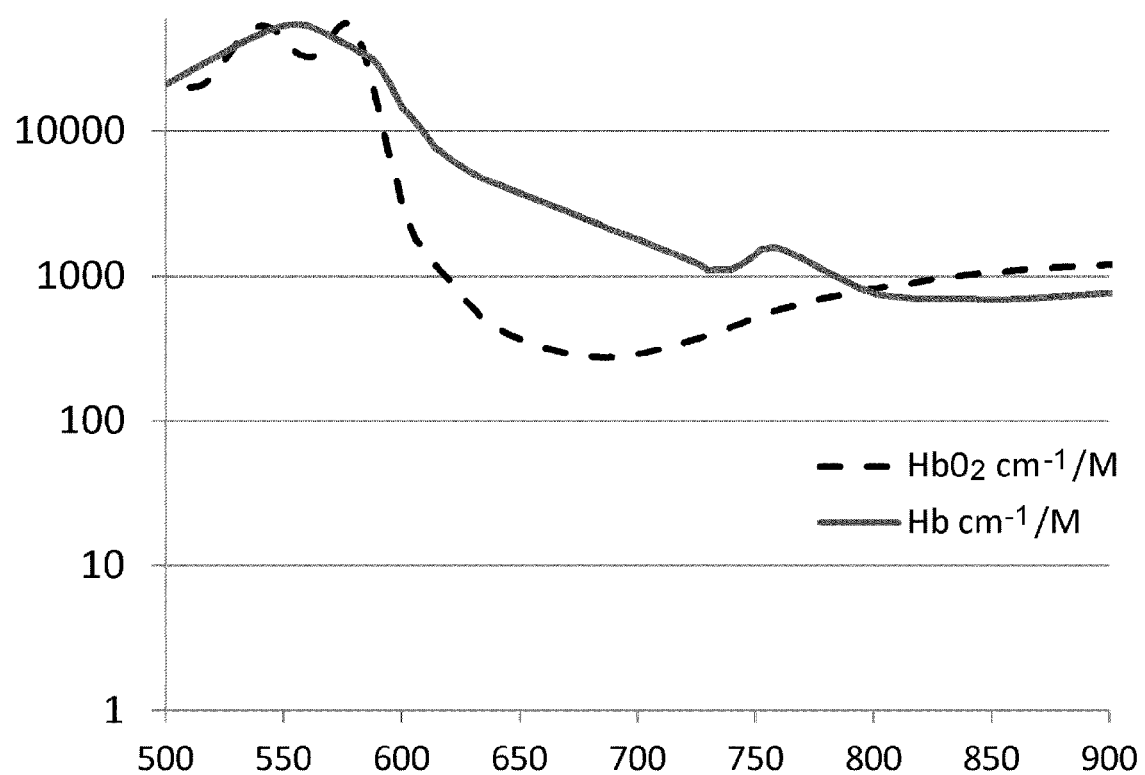
FIG. 7 is a view showing absorption spectra of oxyhemoglobin and deoxyhemoglobin.
Figure 8:
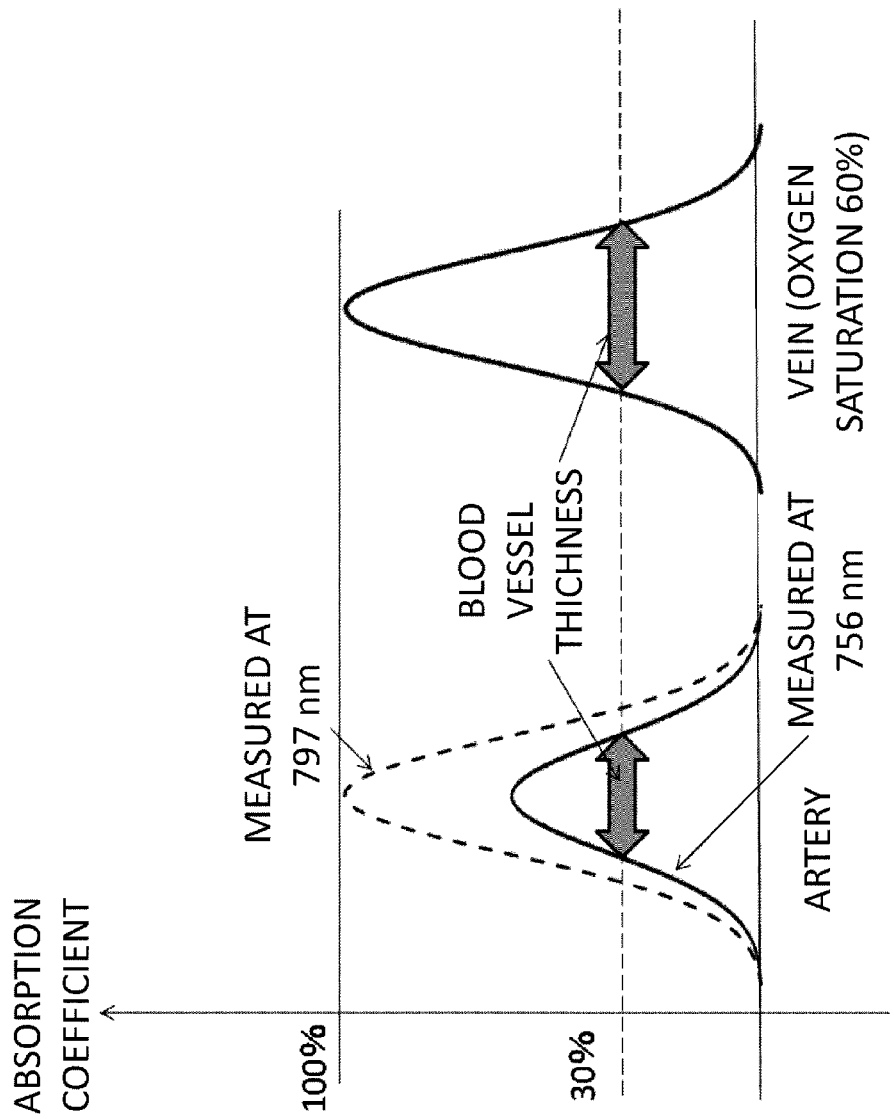
FIG. 8 is a view showing differences in the appearance of an artery and a vein depending on a wavelength.
Figure 9:
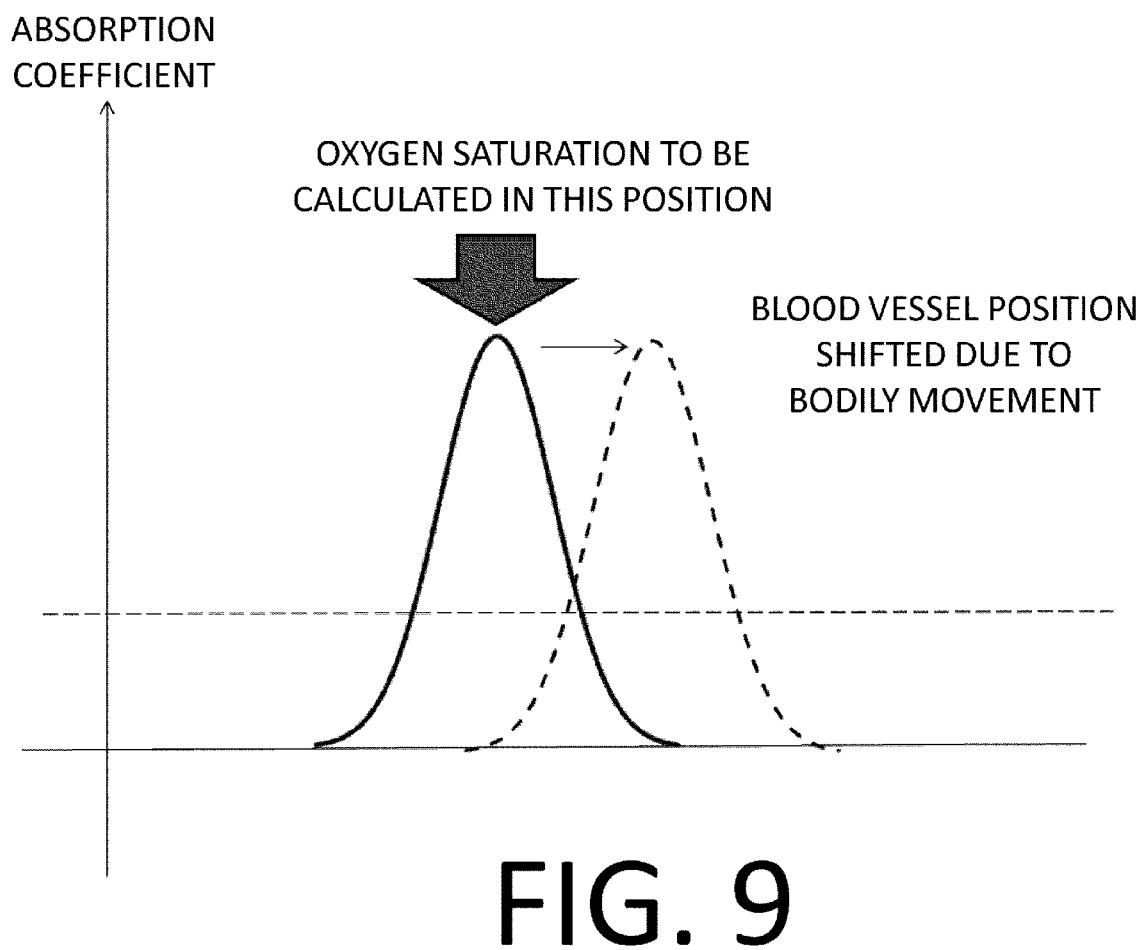
FIG. 9 is a view showing a deviation in an absorption coefficient distribution due to bodily movement.

The light source 1 may be any light source that generates pulsed light (PLS) in an order of nanoseconds at a wavelength of at least 700 nm. As shown in FIG. 6, with a light source having a wavelength of not more than 700 nm, a large amount of absorption occurs in hemoglobin, collagen, and so on such that the light cannot reach a sufficiently deep portion of the object interior. It is therefore desirable to use a wavelength of at least 700 nm. A laser is preferable for obtaining a large output, but a light emitting diode or the like may be used instead of a laser. Various types of lasers, such as a solid state laser, a gas laser, a dye laser, or a semiconductor laser, may be used as the laser. A timing, a waveform, an intensity, and so on of the irradiation are controlled by a light source control unit, not shown in the drawing.

In the present invention, light having a plurality of wavelengths is used. To generate the light having the plurality of wavelengths, for example, a single variable wavelength light source may be used or a plurality of light sources corresponding to the respective wavelengths may be prepared. The light having the plurality of wavelengths can be emitted individually at different timings.

Further, to guide the light from the light source to the object, optical members such as a mirror that reflects the light, a lens that changes the shape of the light by condensing or expanding the light, a prism that disperses, refracts, or reflects the light, an optical fiber that propagates the light, or a diffuser plate may be used.

The light may be emitted onto the object from the same side as the ultrasound probe or an opposite side. The object may also be irradiated from both sides.

(Wavelength Selection Unit)

The wavelength selection unit 6 selects the wavelength of the pulsed light to be emitted from the light source 1, and transmits selected wavelength information (SEL) to the image reconstruction unit.

(Ultrasound Probe)

The ultrasound probe 3 is an acoustic detector having at least one element for receiving an acoustic wave (an ultrasound wave). In a type of probe where a plurality of elements are arranged in a plane of the ultrasound probe, signals from a plurality of positions can be obtained at once. As a result, a reception time can be shortened, and effects generated by vibration and the like in the object can be reduced.

The ultrasound probe receives the ultrasound wave (USW) constituting the acoustic wave, amplifies the received ultrasound wave, converts the ultrasound wave into an electric signal, and then outputs the electric signal. The element used in the ultrasound probe may be a conversion element that uses piezoelectricity, a conversion element that uses optical resonance, a conversion element that uses capacitance variation, and so on. Any ultrasound probe that can receive an acoustic wave and convert the received acoustic wave into an electric signal may be used.

(Image Reconstruction Unit)

The electric signal (SIGNAL) from the ultrasound probe 3 is input into the image reconstruction unit 4. The image reconstruction unit 4 performs image reconstruction using the input electric signal, and generates absorption coefficient distribution image information (ABS), which is image data representing a distribution of the absorption coefficients of the object interior. At this time, processing can be performed for each wavelength in accordance with the selected wavelength information (SEL) received from the wavelength selection unit 6. Processing such as amplification and digital conversion is preferably implemented either before or after the electric signal is input into the image reconstruction unit 4. The image reconstruction unit corresponds to an absorption coefficient distribution generator according to the present invention.

Back projection or the like in a time domain or a Fourier domain, for example, which is typically used in a tomography technique, may be used as an image reconstruction algorithm for generating the image data. In a case where it is possible to spend a large amount of time on reconstruction, an image reconstruction method such as an iterative method that uses repetitive processing may be employed. Representative examples of PAT image reconstruction methods include a Fourier transform method, a universal back projection method, and a filtered back projection method.

(Image Memory)

The image memory 5 is a location for recording the absorption coefficient distribution image information (ABS) generated by the image reconstruction unit 4. The recorded information is output to the blood vessel position determining unit 8, the organism characteristics distribution calculator 9, and the display unit 11 as required.

(Organism Characteristics Distribution Calculator)

The organism characteristics distribution calculator 9 is an organism characteristics distribution calculator for generating organism characteristics distribution information (DST). The organism characteristics distribution information (DST) may be an oxygen saturation distribution, a glucose distribution, or a collagen distribution.

Using the oxygen saturation as an example, a method of calculating the organism characteristics distribution information will be described. Equation (1) shows a formula for determining an absorption coefficient $\mu_a$ ($\lambda_i$) of a blood vessel, measured at a certain wavelength $\lambda_i$. The absorption coefficient $\mu_a$ ($\lambda_i$) is the sum of a product of an absorption coefficient $\varepsilon_{HbO2}$ ($\lambda_i$) and a concentration [HbO$_2$] of oxyhemoglobin and a product of an absorption coefficient $\varepsilon_{HbR}$ ($\lambda_i$) and a concentration [HbR] of deoxyhemoglobin.

[Math. 1]

$$\mu_a(\lambda_i)=\varepsilon_{HbO2}(\lambda_i)\cdot[HbO_2]+\varepsilon_{HbR}(\lambda_i)\cdot[HbR] \quad (1)$$

As a result, the oxyhemoglobin concentration [HbO$_2$] and the deoxyhemoglobin concentration [HbR] in a certain position (x, y, z) are determined as shown in Equation (2).

[Math. 2]

$$\begin{bmatrix}[HbO_2]\\ [HbR]\end{bmatrix}_{(x,y,z)} = (E^T E)^{-1} E^T \cdot M_a(x, y, z) \quad (2)$$

Here, E and $M_a$ (x, y, z) are expressed by Equation (3) below.

[Math. 3]

$$E = \begin{bmatrix}\varepsilon_{HbO_2}(\lambda_1) & \varepsilon_{HbR}(\lambda_1)\\ \cdots & \cdots\\ \varepsilon_{HbO_2}(\lambda_n) & \varepsilon_{HbR}(\lambda_n)\end{bmatrix},$$

$$M_a(x, y, z) = \begin{bmatrix}\mu_a(\lambda_1, x, y, z)\\ \cdots\\ \mu_a(\lambda_n, x, y, z)\end{bmatrix} \quad (3)$$

where $\mu_a$ ($\lambda_i$, x, y, z) is an absorption coefficient in the (x, y, z) position relative to the wavelength $\lambda_i$.

Hence, an oxygen saturation SO$_2$ in a certain position (x, y, z) is calculated as shown in Equation (4) below.

[Math. 4]

$$SO_{2(x,y,z)} = \frac{[HbO_2]_{(x,y,z)}}{[HbO_2]_{(x,y,z)} + [HbR]_{(x,y,z)}} \quad (4)$$

According to Equation (2), [HbO$_2$] and [HbR] can be obtained from measurement results corresponding to two wavelengths. When measurement results corresponding to three or more wavelengths are used, most probable values of [HbO$_2$] and [HbR], which are equivalent to results obtained using a method of least squares, are obtained.

Hence, when measurement is performed using three or more wavelengths, first, a plurality of wavelength combinations excluding at least one of the measured wavelength results are prepared. A plurality of hemoglobin concentrations may then be calculated using Equation (2) in relation to each wavelength group, whereupon the oxygen saturation is calculated using a method of least squares or an average.

The glucose distribution of blood may be learned instead of the oxygen saturation as the organism characteristics distribution information (DST). A glucose distribution [Glc] is calculated using Equation (5) below.

[Math. 5]

$$\mu_a(\lambda_i)=\varepsilon_{Glc}(\lambda_i)\cdot[Glc] \quad (5)$$

In this case, a glucose concentration distribution is determined from absorption coefficients relating to a single wavelength.

The oxygen saturation or glucose distribution calculation result is greatly affected by a positional precision of the absorption coefficient distribution $\mu_a$ ($\lambda_i$, x, y, z) at each wavelength $\lambda_i$. Therefore, a large error may occur in the oxygen saturation result when the object serving as the measurement subject moves during measurement.

Hence, a method of minimizing the error in the oxygen saturation by intentionally blurring the absorption coefficient distribution $\mu_a$ ($\lambda_i$, x, y, z) may be used. A method of taking an average of peripheral absorption coefficients or a method using a filter may be employed as a method of blurring the absorption coefficients.

(Blood Vessel Position Determining Unit)

The blood vessel position determining unit 8 determines the position of a blood vessel from the absorption coefficient distribution image information created by the image reconstruction unit 4. Determination conditions are stored in the absorber determining condition memory 7. The blood vessel position determining unit 8 accesses the absorber determining condition memory 7 and reads the conditions as required. A method of providing a predetermined threshold in advance and setting a position where the absorption coefficient equals or exceeds the predetermined threshold as the blood vessel position may be used as a determination method. Alternatively, a method of correlating an array or a shape of positions where the absorption coefficient is strong or a shape of an artifact appearing on the periphery of an absorber with blood vessel conditions stored in the absorber determining condition memory 7 and setting a position having a high correlation as the blood vessel position may be used.

An absorption coefficient strength and a correlation threshold for determining the blood vessel position may be stored in the absorber determining condition memory 7, or a noise level may be evaluated and set automatically at an appropriate value. For example, a method of creating a histogram of absorption coefficients on an image and setting a concentration value of absorption coefficients in lower positions than the absorption coefficient of the blood vessel as a noise level, or a method of identifying a range that may be considered as noise and setting an average of the absorption coefficients within that range as the noise level may be used. Alternatively, a button for adjusting the predetermined threshold may be provided on the display unit so that the predetermined threshold can be adjusted by a technician while referring to a display screen. Blood vessel position determination information (POS) is transmitted to the absorber determining condition memory 7. When a rewritable memory is used as the absorber determining condition memory 7, modified conditions can be recorded therein.

(Image Trimming Unit)

The image trimming unit 10 inputs an absorption coefficient information distribution image determined using the oxygen saturation information from the organism characteristics distribution calculator 9 and the blood vessel position from the blood vessel position determining unit 8. An oxygen saturation image (IMG) is created to emphasize the oxygen saturation information in the blood vessel position on the absorption coefficient information image, and the created oxygen saturation image (IMG) is output to the display unit 11. The image trimming unit 10 may also output an image formed by synthesizing the emphasized oxygen saturation with the absorption coefficient distribution image.

(Display Unit)

The image output by the image trimming unit 10 and the reconstructed absorption coefficient distribution image are displayed. An MIP (Maximum Intensity Projection) image display method or a slice image display method may be used as a display method, but another display method may also be applied. For example, a method of displaying a 3D image from a plurality of different directions may be applied. Alternatively, a method in which a user modifies an incline or a display region of the displayed image, a window level, and a window width while checking the display may be used. Further, a method of displaying the oxygen saturation image and the absorption coefficient distribution image side by side or a method of synthesizing the display positions of the displayed images may be used.

Furthermore, an input unit such as a button with which the blood vessel determining conditions used by the blood vessel position determining unit 8 in the blood vessel position determination can be adjusted while checking the displayed image may be disposed on the display unit.

(Information Processing Device)

The processing of the respective blocks described above may be realized as a control method for causing an information processing device 12 such as a PC to execute a predetermined program, for example. The information processing device transmits control content to the respective blocks through a control wire, not shown in the drawings, wirelessly, or by another method. If necessary, the user may issue instructions to the information processing device or the respective blocks.

First Embodiment

An example of the photoacoustic diagnosis apparatus according to the present invention will now be described.

Light of two wavelengths (756 nm, 797 nm) was emitted along a single optical path using a Ti:S (titanium sapphire laser) as a light source. An optical density of the wavelengths was 15 mJ/cm$^2$. Nd:YAG laser light (pulsed light in an order of nanoseconds at a wavelength of 1064 nm) was used to excite the Ti:S. Measurement was performed using wavelengths of at least 700 nm that reached a deep portion of the object.

First, light having a wavelength of 797 nm was used. This wavelength is in the vicinity of the wavelength at which the absorption coefficients of the two types of hemoglobin are equal in a region of at least 700 nm. The light having the 797 nm wavelength corresponds to light having a first wavelength according to the present invention. According to our knowledge, a wavelength region in which the absorption coefficients may be considered equal is preferably a wavelength region in which the thickness of the blood vessel varies by less than ±10% when an absorption coefficient distribution image obtained through measurement at a wavelength in this region is trimmed using a value that is larger than a noise value of the absorption coefficient distribution image by an appropriate degree as a threshold. In this embodiment, wavelengths in a wavelength region of 778 nm to 950 nm, in which the blood vessel thickness varied by less than ±10% when trimming was performed using 30% of a maximum absorption coefficient of the blood vessel position as a threshold, were used.

Next, light having a wavelength of 756 nm, with which the absorption coefficients of the two types of hemoglobin differ, was used. A peak of the absorption coefficient of deoxyhemoglobin appears at the 756 nm wavelength, and therefore an absorption coefficient difference between the two types of hemoglobin is large. This light corresponds to light having a second wavelength according to the present invention. By selecting light having a wavelength such as the 756 nm wavelength, with which the difference between the absorption coefficients of the two types of hemoglobin is large and similar absorption coefficients to the absorption coefficients relating to the light having the 797 nm wavelength are obtained, when calculating the oxygen saturation, it is possible to obtain the oxygen saturation with a high degree of precision.

Using the light described above, an object having a thickness of no less than 50 mm in a perpendicular direction to a reception surface of the ultrasound probe was measured.

First, the object was irradiated with light having the 797 nm wavelength (corresponding to S201 in FIG. 2), whereupon a photoacoustic wave from the object was received by the ultrasound probe (S202). Since the used wavelength was no smaller than 700 nm, at which the absorption coefficients of melanin and hemoglobin are low, it was possible to measure a photoacoustic wave from a deep portion of at least 25 mm with sufficient strength. An absorption coefficient distribution image A was then created using an obtained photoacoustic signal (S203). Reconstruction was performed using a back projection method in a time domain.

Measurement was then performed similarly using the 756 nm wavelength, whereupon an absorption coefficient distribution image B was creared (S204 to S206).

Next, the oxygen saturation was calculated using the created absorption coefficient distributions A, B (S207). At this time, an error in the oxygen saturation caused by positional deviation between the images was suppressed by averaging the absorption coefficient distributions at 1.25 mm in a thickness direction.

Next, the blood vessel position was determined by setting an absorption coefficient equaling or exceeding a threshold of the absorption coefficient distribution image A as a blood vessel (S208). The threshold was set at a value of 30% of the maximum absorption coefficient. A value at which it was possible to trim noise in the absorption coefficient distribution image sufficiently was selected as the threshold.

Oxygen saturation information in positions other than the blood vessel position was then set at zero in order to emphasize the calculated oxygen saturation information in the blood vessel position, whereupon the resulting image was displayed (S209 to S210).

Next, effects obtained by implementing the present invention will be described. FIG. 5A is a view showing the oxygen saturation in a simulated organism in a region of 30 mm in an x direction, 46 mm in a y direction, and 50 mm in a z direction. The simulated organism had a similar acoustic velocity and similar absorption coefficients and dispersion coefficients to the organism. Simulated blood vessels having oxygen saturations corresponding respectively to an artery and a vein were disposed in central positions of 25 mm in a depth direction z of the simulated organism. The simulated vein (indicated by "P" in the drawing) and the simulated artery (indicated by "A" in the drawing) are shown respectively on a right side and a left side of FIG. 5A. The simulated organism was irradiated with various types of light, and photoacoustic waves generated as a result were measured using a 3 cm×4.6 cm probe disposed parallel to an xy plane, whereby an absorption coefficient distribution image and an oxygen saturation were obtained.

FIG. 5D shows the absorption coefficient distribution measured at the 797 nm wavelength. FIG. 5E shows a trimmed oxygen saturation image obtained from the absorption coefficient distribution at the 797 nm wavelength. FIG. 5B shows the absorption coefficient distribution measured at the 756 nm wavelength. FIG. 5C shows a trimmed oxygen saturation image obtained from the absorption coefficient distribution at the 756 nm wavelength.

The simulated blood vessels disposed in the 25 mm depth position in the z direction can be recognized in FIGS. 5B to 5E, and it was therefore confirmed that an absorption coefficient distribution image can be measured up to a deep portion of 25 mm of the object at either wavelength. When the blood vessel positions were determined using the absorption coefficient distribution image B corresponding to light having the 756 nm wavelength, at which the absorption coefficient of oxyhemoglobin is smaller than the absorption coefficient of deoxyhemoglobin, the vein became thicker and the artery became narrower on the oxygen saturation image shown in FIG. 5C. Further, a part of the artery disappeared.

When, on the other hand, the blood vessel positions were determined using the absorption coefficient distribution image A corresponding to light having the 797 nm wavelength, at which the absorption coefficients of the two types of hemoglobin are equal, a full width at half maximum of both the vein and the artery was no more than ±5% on the formed image, and therefore the vein and the artery were displayed substantially equally. Hence, it was confirmed that when blood vessel positions are determined using an absorption coefficient distribution relating to a wavelength of no less than 700 nm at which the absorption coefficients of the two types of hemoglobin are equal, veins and arteries in a deep portion of the object have a similar appearance.

Note that in this embodiment, the oxygen saturation was calculated using two wavelengths, but the oxygen saturation may be calculated using three or more wavelengths. In this case, the wavelength A (797 nm) at which the absorption coefficients of oxyhemoglobin and deoxyhemoglobin are equal, the wavelength B (756 nm) at which the respective absorption coefficients are different, and a plurality of wavelengths (or a single wavelength; wavelengths other than 797 nm and 756 nm) not restricted by a magnitude relationship between the absorption coefficients are used.

Second Embodiment

Figure 3:
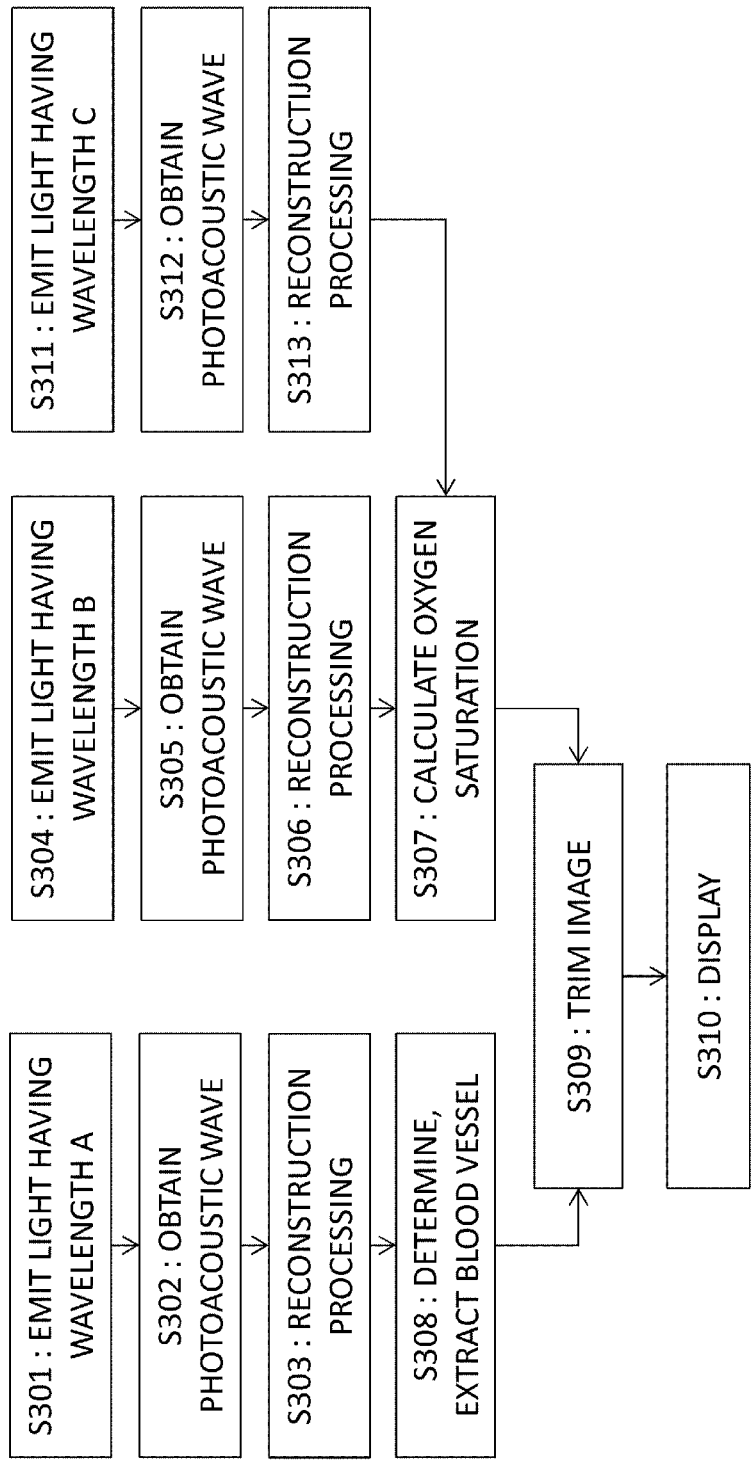
FIG. 3 is a flowchart showing processing according to a second embodiment.

In the first embodiment, an apparatus that obtains the oxygen saturation using the absorption coefficient distribution relating to the wavelength A at which the absorption coefficients of oxyhemoglobin and deoxyhemoglobin are equal was described. In this embodiment, a photoacoustic apparatus that calculates the oxygen saturation without using the absorption coefficient distribution of the wavelength A will be described as an example. FIG. 3 is a flowchart showing this embodiment. Here, parts that differ from the first embodiment will be described in particular detail.

In this embodiment, light sources having a wavelength of 797 nm as the wavelength A, a wavelength of 756 nm as the wavelength B, and a wavelength of 825 nm as a wavelength C were used. The wavelength B and the wavelength C are wavelengths at which the absorption coefficients of the two types of hemoglobin are different. A Ti:S laser was used as the light source, and the object was irradiated with light transmitted along a single optical path.

First, in Step S301, the object was irradiated with light having the wavelength A, whereupon a photoacoustic wave was obtained in Step S302 and image reconstruction using an obtained acoustic signal was performed in Step S303.

Next, in Step S304, the object was irradiated with light having the wavelength B, whereupon a photoacoustic wave was obtained in Step S305 and image reconstruction was performed in Step S306.

Next, in this embodiment, the object was irradiated with light having the wavelength C in Step S311, whereupon a photoacoustic wave was obtained in Step S312 and image reconstruction was performed in Step S313.

In Step S307, the oxygen saturation was calculated using absorption coefficient distribution images B, C relating to the wavelengths B, C at which the absorption coefficients of the two types of hemoglobin are different. At 756 nm, i.e. the wavelength B, the absorption coefficient of deoxyhemoglobin is higher than the absorption coefficient of oxyhemoglobin, and at 825 nm, i.e. the wavelength C, the absorption coefficient of oxyhemoglobin is higher than the absorption coefficient of deoxyhemoglobin. By selecting wavelengths such as the 756 nm and 825 nm wavelengths, at which the magnitude relationship between the absorption coefficients of the two types of hemoglobin are reversed and similar absorption coefficients to those relating to the wavelength A are obtained, the oxygen saturation can be calculated with an even higher degree of precision.

In Step S308, the blood vessel position was determined from the absorption coefficient distribution image relating to the wavelength A. A threshold was provided, and a position having an absorption coefficient equaling or exceeding the threshold was set as a blood vessel. The threshold was set at a value of 30% of the maximum absorption coefficient.

In Step S309, an image emphasizing the oxygen saturation in the blood vessel position was created on the basis of the oxygen saturation information and blood vessel position information calculated in S307 and S308. The oxygen saturation in the blood vessel position was emphasized by removing oxygen saturations in positions other than the blood vessel position.

In Step S310, the image obtained in S309 was displayed.

The order of S301 to S303, S304 to S306, and S311 to S313, corresponding to procedures extending from irradiation at the respective wavelengths A, B, and C to reconstruction, may be reversed. Further, reconstruction may be performed after obtaining signals at all of the wavelengths. The procedures of S307 and S308 may also be reversed. Alternatively, the procedures of S301 to S304 and S308 may be performed after completing S307, or vice versa.

Effects of this embodiment will now be described. It was possible to measure an absorption coefficient distribution image up to a deep portion of at least 25 mm of the object at all of the wavelengths A, B, C. When the blood vessel position was determined using the wavelength B, the full width at half maximum of the vein was larger on the obtained image, and when the blood vessel position was determined using the wavelength C, the full width at half maximum of the artery was larger on the obtained image. When the blood vessel position was determined using the wavelength A, however, the full width at half maximum values of both the vein and the artery differed only by approximately ±5% on the obtained image, and therefore the vein and the artery were emphasized to a similar degree. It was therefore confirmed that by determining the blood vessel position using an absorption coefficient distribution relating to a wavelength of no less than 700 nm at which the absorption coefficients of the two types of hemoglobin are equal, veins and arteries in a deep portion of the object have a similar appearance.

Third Embodiment

In the first and second embodiments, measurement of the oxygen saturation in the blood vessel position was described, but in this embodiment, a method of measurement the glucose distribution in the blood vessel position will be described. The following description focuses on parts of this embodiment that differ from the first and second embodiments.

Figure 4:
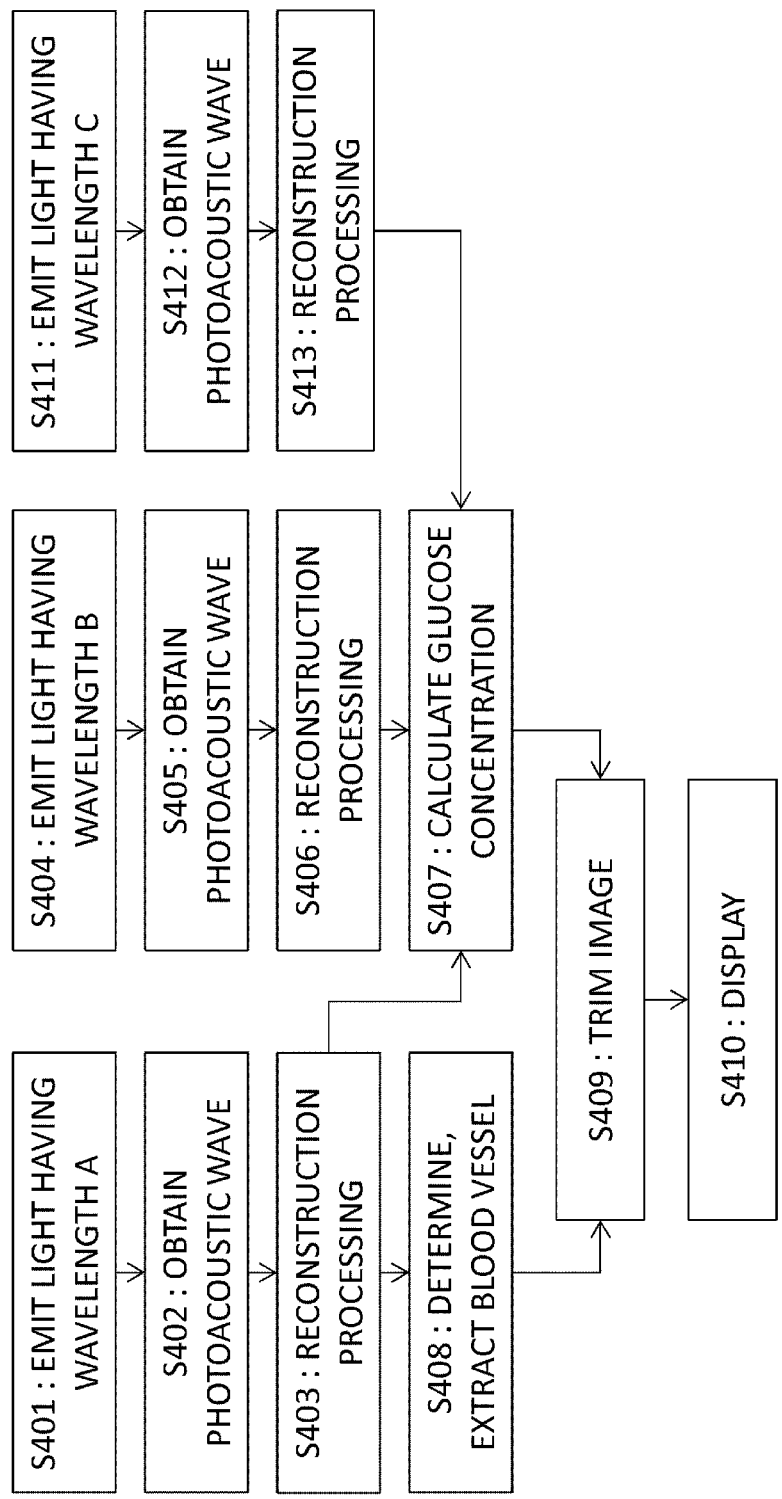
FIG. 4 is a flowchart showing processing according to a third embodiment.

In this embodiment, a total of three wavelengths, namely the wavelength A at which the absorption coefficients of the two types of hemoglobin are equal and two wavelengths B, C for measuring the glucose distribution, were used. FIG. 4 is a flowchart showing this embodiment. The wavelength A is mainly used to identify the blood vessel position. The wavelengths B, C are selected from a range of 700 nm to 1100 nm. This is a wavelength region in which the absorption coefficients of glucose, water, and so on are comparatively low. In principle, the glucose distribution can be calculated by measuring an absorption coefficient distribution relating to a single wavelength, but in this embodiment, the glucose distribution was measured from three wavelengths.

First, light was emitted at the respective wavelengths, whereupon photoacoustic waves were obtained and image reconstruction was performed. Processing of S401 to S403, S404 to S406, and S411 to S413 was executed while varying the wavelength of the light source. In this part, measurement was performed similarly to the second embodiment.

In Step S407, glucose distributions were calculated using the absorption coefficient distributions obtained from the wavelengths A, B, C and the mathematical formula shown in Equation (5). An average of the glucose distributions obtained in relation to the respective wavelengths was then calculated, whereupon a glucose distribution image was created.

In Step S408, the blood vessel position was determined by applying a threshold corresponding to 30% of the maximum absorption coefficient to the absorption coefficient distribution image relating to the wavelength A and setting an absorbent having an absorption coefficient equaling or exceeding the threshold as a blood vessel.

In Step S409, the glucose distribution image obtained in S407 was adjusted on the basis of the blood vessel position information obtained in S408 such that the blood vessel position was emphasized by setting distributions in positions other than the blood vessel position at zero.

Effects of this embodiment will now be described. It was possible to measure an absorption coefficient distribution image up to a deep portion of at least 25 mm of the object, and it was confirmed that on the displayed glucose distribution, both the vein and the artery appeared as blood vessels having an identical thickness.

Fourth Embodiment

In the embodiments described above, measurement is performed using light having a plurality of wavelengths, and therefore time differences occurs between the measurement operations performed at the respective wavelengths. If the measurement position of the object shifts due to bodily movement during the time difference, positional deviation may occur among the plurality of reconstructed images. As a result, the positioning and trimming precision, for example, may decrease such that positions of the vein and the artery are not aligned, leading to blurring and so on of the organism characteristics distribution image.

Figure 10A:
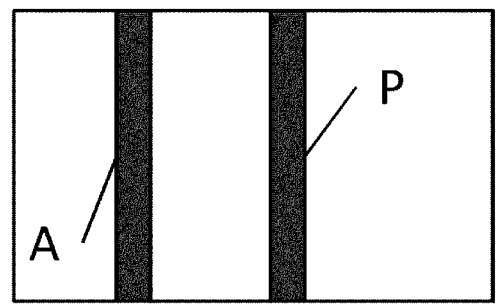
FIGS. 10A to 10C are views showing a deviation occurring during reconstructed image synthesis due to bodily movement.
Figure 10B:
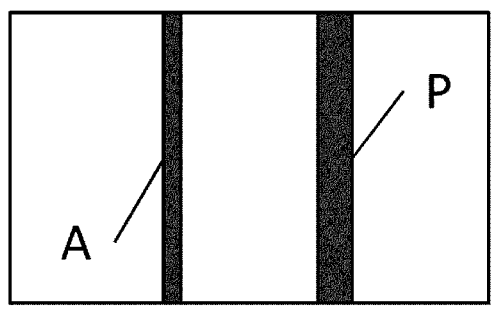
Figure 10C:

FIG. 10 shows this phenomenon. FIG. 10A is an absorption coefficient distribution obtained when a measurement region of the object is irradiated with light having the 797 nm wavelength, at which the absorption coefficients of the two types of hemoglobin are substantially equal. An image P derived from a vein existing in the measurement region and an image A derived from an artery existing in the measurement region can be seen. FIG. 10B is an absorption coefficient distribution obtained when the measurement region is irradiated with light having the 756 nm wavelength, at which the absorption coefficients of the two types of hemoglobin are different. If, at this time, bodily movement occurs while performing measurement at a different wavelength, the positions of the blood vessels shift when the images are synthesized, as shown in FIG. 10C.

To reduce the effect of bodily movement, conditions such as the threshold used by the blood vessel position determining unit to determine the blood vessel positions may be adjusted. Alternatively, corresponding measurement positions between a plurality of reconstructed images may be determined and formed into images by comparing characteristic amounts, tracking motion vectors, performing positioning using markers, and so on.

In this embodiment, a method of increasing a size of a light absorber on at least one image when a position of a light absorber shifts between a plurality of images due to bodily movement, thereby causing the light absorber to overlap the light absorber of the other images on a synthesized image, will be described. A method of reducing a resolution in an image space is used to increase the size of the light absorber. In so doing, the light absorber can be increased in size so as to appear blurred. When a method of reducing the resolution is used, there is no need to learn the positional deviation in each target region (a voxel, a pixel, or the like) of the object, and therefore a calculation amount can be suppressed. In the present invention, the method of reducing the resolution in the image space is a method of making the image of the light absorber appear blurred by reducing variation between absorption coefficient values in adjacent positions (between voxels or between pixels) on the absorption coefficient distribution.

A flow of a series of processes executed in this embodiment will now be described. First, the image reconstruction unit creates absorption coefficient distribution images from photoacoustic wave measurement results obtained at respective wavelengths, similarly to the embodiments described above. The blood vessel position determining unit then determines the blood vessel positions from the absorption coefficient distribution images corresponding to the respective wavelengths, and learns roughly an amount of positional deviation between the images. Here, there is no need to learn the positional deviation at a detailed level (a voxel, a pixel, or the like, for example), and a rough deviation amount from which a degree of resolution reduction can be determined is sufficient. Examples of methods for learning the deviation amount include analysis of the reconstructed image, analysis performed by mechanically measuring or optically projecting the bodily movement, manual input by the user, and so on, but any method may be used. When optical projection is used, positions of marks that may form features on the object may be compared, or markers may be disposed. Further, a positional deviation determining unit that determines the presence or absence of positional deviation and learns the deviation amount may be provided.

The degree of resolution reduction is then determined on the basis of the learned deviation amount. This determination may be performed by the blood vessel position determining unit or by transmitting the deviation amount to the organism characteristics distribution calculator, the image trimming unit, or another added block. When the resolution of only one of the images is to be reduced, processing is performed at least such that the blood vessel on the image not subjected to resolution reduction is included in the image of the blood vessel that appears larger due to resolution reduction.

Various methods of filter-processing the image may be used to reduce the resolution. For example, the image of the blood vessel or the like may be blurred by applying a moving average filter or a Gaussian filter to the reconstructed image. The degree of resolution reduction can be modified by adjusting an application range of the filter or a filter coefficient. For example, a relationship between the amount of positional deviation and the degree of resolution reduction may be determined in advance and stored in the form of a table or a relational expression. Alternatively, the degree of reduction may be modified on an identical reconstructed image in accordance with the size of the absorber (the thickness of the blood vessel image).

Figure 11A:
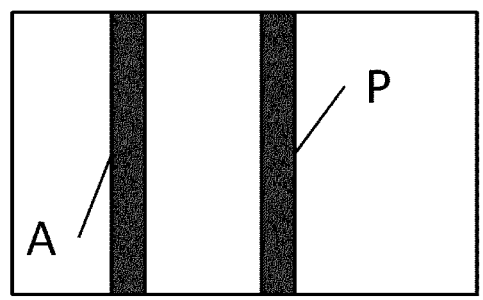
FIGS. 11A to 11C are views showing reconstructed image synthesis according to a fourth embodiment.
Figure 11B:
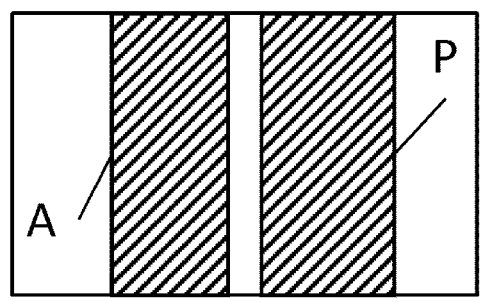
Figure 11C:
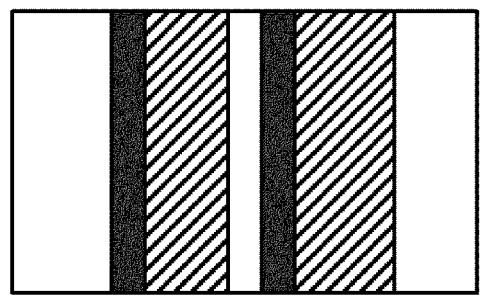

FIG. 11 shows results obtained when this embodiment is applied. FIG. 11A is an identical absorption coefficient distribution to that of FIG. 10A, which is obtained when light having the 797 nm wavelength is emitted. FIG. 11B is an image obtained when resolution reduction processing is implemented on the image shown in FIG. 10B, which is generated when positional deviation occurs due to bodily movement. As shown in the drawing, the blood vessel images are blurred and appear larger. The extent of the resolution reduction processing is determined such that when synthesis processing is performed, the light absorbers of the two images overlap each other, as shown in FIG. 11C. The image trimming unit may perform trimming in the range of the blood vessel images shown in FIG. 11A either before or after the images are synthesized.

By applying the processing according to this embodiment, when measurement positions shift due to bodily movement, the organism characteristics distribution images representing the oxygen saturations can be synthesized with a certain degree of precision. Further, by determining the blood vessel position to be used during trimming on the basis of a reconstructed image corresponding to light having a wavelength at which the absorption coefficients of the two types of hemoglobin are equal during display on the display unit, easily viewable organism characteristics distribution information reflecting the actual thickness of the blood vessel can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-084794, filed on Apr. 6, 2011, which is hereby incorporated by reference herein in its entirety.

The invention claimed is:

1. An information processing apparatus for acquiring an object information of an organism comprising:
   an input unit configured to specify an oxygen saturation criteria to determine a blood vessel type based on an input from a user;
   a first unit configured to obtain a blood vessel position using a first reconstructed image data obtained from an acoustic wave generated by irradiating an object with light of a first wavelength under an isosbestic condition within 778 nm to 950 nm;
   a second unit configured to obtain characteristics distribution information based on at least two acoustic waves generated in response to a couple of light irradiations in association with at least two different wavelengths within 778 nm to 950 nm and the criteria specified by the user; and
   a display unit configured to display the characteristics distribution information associated with the blood vessel position on a display.

2. The information processing apparatus according to claim 1, wherein the characteristics distribution information is oxygen saturation distribution information.

3. The information processing apparatus according to claim 1, wherein the characteristics distribution information is glucose distribution information or collagen distribution information.

4. The information processing apparatus according to claim 1, wherein the at least two different wavelengths include a wavelength at which an absorption coefficient of oxyhemoglobin and an absorption coefficient of deoxyhemoglobin are different.

5. The information processing apparatus according to claim 1, further comprising a third unit configured to acquire, as the first reconstructed image data, absorption coefficient distribution information corresponding to the light of the first wavelength.

6. The information processing apparatus according to claim 1, wherein the at least two different wavelengths include a first wavelength and a second wavelength, wherein the second wavelength is different from the first wavelength, and
   wherein the information processing apparatus further comprises a third unit configured to acquire the characteristics distribution information on the basis of the first reconstructed image data and a second reconstructed image data, wherein the second reconstructed image data is obtained from an acoustic wave generated by irradiating an object with light of the second wavelength.

7. The information processing apparatus according to claim 6, wherein the third unit is further configured:
   to acquire, as the first reconstructed image data, a first absorption coefficient distribution information corresponding to the light of the first wavelength;
   to acquire, as the second reconstructed image data, a second absorption coefficient distribution information corresponding to the light of the second wavelength; and to acquire the characteristics distribution information on the basis of the first absorption coefficient distribution information and the second absorption coefficient distribution information.

8. The information processing apparatus according to claim 6, wherein the third unit is further configured to acquire the characteristics distribution information after reducing a resolution of at least one of the first reconstructed image data and the second reconstructed image data.

9. The information processing apparatus according to claim 8, wherein the first unit is configured to identify the blood vessel position using the first reconstructed image data before resolution reduction.

10. The information processing apparatus according to claim 1, wherein the display unit is configured to selectively display, on the display unit, a part of the characteristics distribution information distanced at least 25 mm from a receiving unit which receives the acoustic wave.

11. The information processing apparatus according to claim 1, wherein the first unit is configured to identify the blood vessel position as a position at which a value of the first reconstructed image data is within a predetermined range.

12. The information processing apparatus according to claim 1, wherein the at least two different wavelengths includes the first wavelength.

13. The information processing apparatus according to claim 1, wherein the blood vessel type is any one of a vein and an artery.

14. The information processing apparatus according to claim 1, wherein the oxygen saturation criteria includes a blood vessel determining condition on which the blood vessel type is to be determined.

15. The information processing apparatus according to claim 1, wherein the first wavelength is approximately 797 nm at which there is no more than a 10% difference between an absorption coefficient of oxyhemoglobin and an absorption coefficient of deoxyhemoglobin.

16. The information processing apparatus according to claim 1, wherein the first wavelength is 797 nm.

17. An information processing method for acquiring an object information of an organism comprising:
    specifying an oxygen saturation criteria to determine a blood vessel type based on an input from a user;
    obtaining a blood vessel position using a first reconstructed image data obtained from an acoustic wave generated by irradiating an object with light of a first wavelength under an isosbestic condition within 778 nm to 950 nm;
    obtaining characteristics distribution information based on at least two acoustic waves generated in response to a couple of light irradiations in association with at least two different wavelengths within 778 nm to 950 nm and the criteria specified by the user; and
    displaying the characteristics distribution information associated with the blood vessel position on a display.

18. The information processing method according to claim 17, wherein the characteristics distribution information is oxygen saturation distribution information.

19. The information processing method according to claim 17, wherein the at least two different wavelengths include a first wavelength and a second wavelength, wherein the second wavelength is different from the first wavelength, and
    wherein the information processing method further comprises acquiring the characteristics distribution information on the basis of the first reconstructed image data and a second reconstructed image data, wherein the second reconstructed image data is obtained from an acoustic wave generated by irradiating an object with light of the second wavelength.

20. The information processing method according to claim 19, wherein acquisition of the characteristics distribution is performed after reducing a resolution of at least one of the first reconstructed image data and the second reconstructed image data.

21. The information processing method according to claim 20, wherein obtaining of the blood vessel position is performed using the first reconstructed image data before resolution reduction.

22. The information processing method according to claim 20, wherein obtaining the blood vessel position comprises determining a position at which a value of the first reconstructed image data is within a predetermine range, and identifying the determined position as the blood vessel position.

23. The information processing method according to claim 17, wherein the blood vessel type is any one of a vein and an artery.

24. The information processing method according to claim 17, wherein the oxygen saturation criteria includes a blood vessel determining condition on which the blood vessel type is to be determined.

25. The information processing method according to claim 17, wherein the first wavelength is approximately 797 nm at which there is no more than a 10% difference between an absorption coefficient of oxyhemoglobin and an absorption coefficient of deoxyhemoglobin.

26. The information processing method according to claim 17, wherein the first wavelength is 797 nm.

27. A non-transitory computer-readable medium storing a program which causes a computer to execute the method of claim 17.

* * * * *